United States Patent
Gagnon

(10) Patent No.: US 6,388,244 B1
(45) Date of Patent: May 14, 2002

(54) VIRTUAL CONTOURING FOR TRANSMISSION SCANNING IN SPECT AND PET STUDIES

(75) Inventor: Daniel Gagnon, Twinsburg, OH (US)

(73) Assignee: Philips Medical Systems (Cleveland), Inc., Highland Heights, OH (US)

( * ) Notice: Subject to any disclaimer, the term of this patent is extended or adjusted under 35 U.S.C. 154(b) by 0 days.

(21) Appl. No.: 09/531,840

(22) Filed: Mar. 20, 2000

(51) Int. Cl.[7] .............................................. H01L 27/00
(52) U.S. Cl. ............................... 250/208.1; 250/363.04
(58) Field of Search ........................ 250/208.1, 363.02, 250/363.03, 363.04, 363.05, 234, 235; 382/131, 132; 128/665

(56) References Cited

U.S. PATENT DOCUMENTS

| 5,638,817 A | * | 6/1997 | Morgan et al. | 128/653.1 |
| 5,717,212 A | | 2/1998 | Fulton et al. | 250/363.5 |
| 5,834,779 A | | 11/1998 | Shao et al. | 250/363.03 |
| 5,900,636 A | | 5/1999 | Nellemann et al. | 250/363.04 |
| 6,008,493 A | | 12/1999 | Shao et al. | 250/363.04 |

FOREIGN PATENT DOCUMENTS

| EP | 962786 A1 | 12/1999 |
| EP | 982603 A2 | 3/2000 |

OTHER PUBLICATIONS

"Attenuation Correction in PET Using Single Photon Transmission Measurement", DeKemp, et al., Med. Phys. 21 (6), Jun. 1994, pp. 771–778.

"IRIX™ Variable Angle, Triple–Detector Nuclear Imaging System", Picker Advertising Brochure, Jul. 1999, pp. 1–4.

"Beacon™ Non–Uniform Attenuation Correction" Picker Advertising Brochure, Aug. 1999, pp. 1–2.

"AXIS™ Variable Angle, Dual–Detector Nuclear Imaging System" Picker Advertising Brochure, Jul. 1999, pp. 1–4.

\* cited by examiner

Primary Examiner—Que T. Le
(74) Attorney, Agent, or Firm—Fay, Sharpe, Fagan, Minnich & McKee, LLP

(57) ABSTRACT

A nuclear gamma camera employs a virtual contouring technique in order to maximize the portion of transmission radiation fan beams (32a, 32b) which pass through a subject (12). A plurality of radiation detector heads (20a–20c) having radiation receiving faces and a plurality of radiation sources (30a, 30b) are mounted to a gantry (16). An orbit memory (42) stores clearance offset orbit (45) around the subject and a subject support (10). A tangent calculator (46) calculates virtual lines (48a, 48b) between the radiation sources (30a, 30b) and the corresponding radiation detector heads (20a, 20b). The virtual lines (48a, 48b) correspond to edge rays of the transmission radiation fans (32a, 32b). A shift calculator (50) calculates and sends shift commands to a motor orbit controller (52) which controls rotational and translational drives attached to the detector heads (20a–20c). The detector heads are translated such that the virtual lines (48a, 48b) remain tangent to a predefined contour of the subject throughout rotation of the detector heads about the subject receiving aperture (18). The detected transmission radiation (32a, 32b) is reconstructed (64t) into an attenuation volumetric image representation and used to correct (68) detected emission radiation data. The corrected emission data is then reconstructed (64e) into a volumetric image representation. The virtual contouring minimizes lost rays (40) of transmission radiation and facilitates an artifact-free attenuation volumetric image representation.

21 Claims, 4 Drawing Sheets

VIRTUAL CONTOURING FOR TRANSMISSION SCANNING IN SPECT AND PET STUDIES

BACKGROUND OF THE INVENTION

The present invention relates to the arts of nuclear medicine and diagnostic imaging. It finds particular application in conjunction with gamma or scintillation cameras and will be described with particular reference thereto. It is to be appreciated that the present invention is applicable to single photon emission computed tomography (SPECT), positron emission tomography (PET), whole body nuclear scans, and the detection of radiation for other applications.

Diagnostic nuclear imaging is used to study a radionuclide distribution in a subject. Typically, one or more radiopharmaceuticals or radioisotopes are injected into a subject. The radiopharmaceuticals are commonly injected into the subject's blood stream for imaging the circulatory system or for imaging specific organs which absorb the injected radiopharmaceuticals. Gamma or scintillation camera detector heads, typically including collimators, are placed adjacent to a surface of the subject to monitor and record emitted radiation. Often, the detector heads are rotated or indexed around the subject to monitor the emitted radiation from a plurality of directions. The monitored radiation data from the multiplicity of directions is reconstructed into a three dimensional image representation of the radiopharmaceutical distribution within the subject.

One of the problems with this imaging technique is that photon absorption and scatter by portions of the subject between the emitting radionuclide and the camera heads distort the resultant image. One solution for compensating for photon attenuation is to assume uniform photon attenuation throughout the subject. That is, the subject is assumed to be completely homogeneous in terms of radiation attenuation with no distinction made for bone, soft tissue, lung, etc. This enables attenuation estimates to be made based on the surface contour of the subject. However, human subjects do not cause uniform radiation attenuation, especially in the chest.

In order to obtain more accurate radiation attenuation measurements, a direct measurement is made using transmission computed tomography techniques. In this technique, radiation is projected from a radiation source through the subject. Radiation that is not attenuated is received by detectors at the opposite side. The source and detectors are rotated to collect transmission data concurrently or sequentially with the emission data through a multiplicity of angles. This transmission data is reconstructed into an image representation using conventional tomography algorithms. The radiation attenuation properties of the subject from the transmission computed tomography image are used to correct or compensate for radiation attenuation in the emission data.

Dual and triple head gamma cameras are now equipped for simultaneous collection of transmission and emission data in order to provide enhanced PET and SPECT attenuation correction. Typically, the transmission device consists of a collimated radioactive line source or a point source mounted for movement along a shielded cylinder. The cylinder may be mounted to one or more of the detector heads through a pivoting arm mechanism. In this configuration, the transmission sources are offset from the detector heads, and therefore offset the useful field of view (FOV).

With one or more offset transmission sources, the transmission radiation beam is offset from the center of rotation, i.e. the center of the subject, creating unsampled regions. Because information from the central portion of the subject is critical for an artifact-free reconstruction, detector heads have been shifted laterally so that the transmission fan beams cover the center of the subject. While lateral shifting of the detector heads enables transmission radiation to pass through a central region, some regions of the patient are still undersampled, and some radiation passes through the air missing the patient. In order to minimize a patient's dose of radiation, the transmission radiation source typically generates only a limited number of radiation events per unit time. Wasting a portion of these events or rays reconstructing empty regions next to the patient is inefficient.

In order to eliminate these "lost rays" of transmission radiation, prior art techniques concentrate on moving the patient support vertically and horizontally during data acquisition. This technique is disadvantageous because it leads to patient discomfort, especially in rapid acquisition sequences.

The present invention contemplates a new and improved contouring technique for use with transmission scans which overcomes the above-referenced problems and others.

SUMMARY OF THE INVENTION

In accordance with one aspect of the present invention, a nuclear medicine gamma camera includes a rotating gantry which defines a subject receiving aperture. A plurality of radiation detector heads, which are movably attached to the rotating gantry, rotate about the subject receiving aperture with rotation of the rotating gantry about an axis of rotation. At least one radiation source is mounted to the rotating gantry such that a divergent beam of transmission radiation from the at least one radiation source is directed toward and received by a corresponding detector head positioned across the subject receiving aperture from the radiation source. A rotational drive rotates the plurality of detector heads around the subject receiving aperture and a plurality of translational drives translate independently the plurality of detector heads (i) laterally in directions tangential to the subject receiving aperture and (ii) radially in directions orthogonal to the axis of rotation. An orbit memory stores a predefined orbit which clears a subject disposed in the subject receiving aperture. A tangent calculator calculates the position of a virtual line between the at least one radiation source and an edge of a radiation receiving face of the corresponding detector head which receives transmission radiation from the at least one radiation source. A shift calculator calculates lateral and radial shifts for the plurality of detector heads such that the detector head positions are dynamically adjusted in order to maintain the virtual line tangent to an outer boundary of the subject throughout rotation of the gantry around the subject receiving aperture. A motor orbit controller controls the plurality of translational drives and the rotational drive in accordance with the orbit from the orbit memory and shift inputs from the shift calculator.

In accordance with another aspect of the present invention, a method of diagnostic imaging using a nuclear medicine gamma camera includes placing a subject in a subject receiving aperture and injecting the subject with a radiopharmaceutical. A plurality of radiation sources and corresponding radiation detector heads are positioned about the subject receiving aperture such that the radiation sources are across the subject receiving aperture from their corresponding radiation detector heads. A contour of the subject is obtained and radiation emitted by the injected radiopharmaceutical is detected using the plurality of radiation detector heads. The positions of virtual lines extending from each radiation source to an edge of a radiation receiving face disposed on each corresponding radiation detector head are calculated. The detector heads are shifted laterally such that the virtual lines are tangent to the contour of the subject. Radiation from the radiation sources is transmitted toward the corresponding radiation detector heads positioned across the subject receiving aperture and detected using one of the plurality of radiation detectors. The detected tranmsission and emission radiation is reconstructed into a volumetric image representation.

In accordance with another aspect of the present invention, a nuclear camera system includes a rotating gantry which defines a subject receiving aperture and a plurality of real radiation detector heads movably attached to the rotating gantry. The real detector heads rotate about the subject receiving aperture with rotation of the rotating gantry. A plurality of radiation sources are mounted to the plurality of real detector heads such that transmission radiation from the radiation sources is directed toward and received by the corresponding real detector heads positioned across the subject receiving aperture from the plurality of radiation sources. A plurality of virtual detector heads impose shift restrictions on the real detector heads during rotation about the subject receiving aperture. A rotational drive rotates the real detector heads about the subject receiving aperture and a pair of translational drives translate independently the real detector heads at least one of laterally and radially with respect to the subject receiving aperture. An orbit memory stores a predefined contour of a subject disposed in the subject receiving aperture. A shift calculator calculates shifts in the real detector heads according to the predefined contour of the subject and the shift restrictions imposed by the virtual detector heads. A motor orbit controller controls the translational and rotational drives in response to commands from the shift calculator.

In accordance with another aspect of the present invention, a nuclear camera includes a rotating gantry on which at least first and second detector heads are mounted. The first detector head carries an offset transmission radiation source that projects a fan bean of transmission radiation to the second detector head, where the fan beam extends between edge rays. A rotating drive rotates the rotating gantry continuously or in steps and a radial drive moves the detector heads in a radially inward direction toward a center of rotation of the rotating gantry and a radially outward direction away from the center of rotation. A lateral drive moves the detector heads with a component of motion orthogonal to the radially inward and outward directions. The nuclear camera is controlled by positioning a subject on a subject support with a region of interest at the center of rotation. A clearance offset orbit around and displaced from the subject and subject support is calculated. A subject orbit around the region of interest is calculated and the subject is injected with a radiopharmaceutical. The rotating drive and radial drive are controlled such that the detector heads are maintained tangent to the clearance offset orbit as the detector heads are rotated around the subject. The lateral drive is controlled such that one of the fan beam edge rays is maintained tangent to the subject orbit as the detector heads rotate.

One advantage of the present invention is that it maximizes the fraction of the transmission radiation beam which interacts with the subject.

Another advantage of the present invention is that it provides a full set of transmission correction data.

Another advantage of the present invention resides in that it facilitates reduction of the radiation dose.

Other benefits and advantages of the present invention will become apparent to those skilled in the art upon a reading and understanding of the preferred embodiment.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
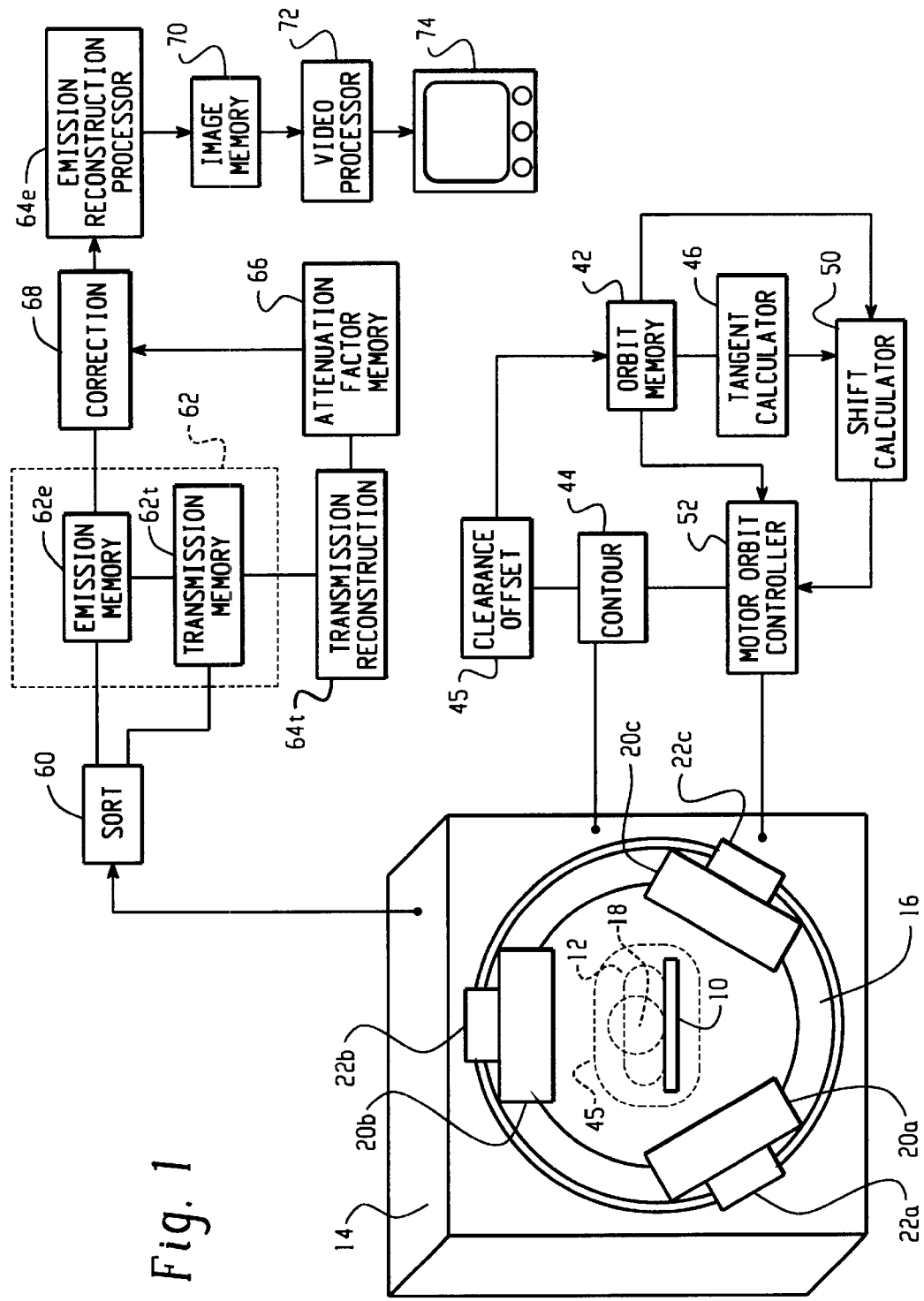
FIG. 1 is a diagrammatic illustration of a nuclear medicine gamma camera in accordance with aspects of the present invention.

With reference to FIG. 1, a diagnostic imaging apparatus includes a subject support 10, such as a table or couch, which supports a subject 12 being examined and/or imaged. The subject 12 is injected with one or more radiopharmaceuticals or radioisotopes such that emission radiation is emitted therefrom. Optionally, the subject support 10 is selectively height adjustable so as to center the subject 12 at a desired height, e.g., the volume of interest is centered. A first or stationary gantry 14 rotatably supports a rotating gantry 16. The rotating gantry 16 defines a subject receiving aperture 18. In a preferred embodiment, the first gantry 14 is moved longitudinally along the subject support 10 so as to selectively position regions of interest of the subject 12 within the subject receiving aperture 18. Alternately, the subject support 10 is advanced and retracted to achieve the desired positioning of the subject 12 within the subject receiving aperture 18.

Detector heads 20a, 20b, 20c are individually positionable on the rotating gantry 16. The detector heads 20a–20c also rotate as a group about the subject receiving aperture 18 (and the subject 12 when received) with the rotation of the rotating gantry 16. The detector heads 20a–20c are radially and circumferentially adjustable to vary their distance from the subject and spacing on the rotating gantry 16, as for example, in the manner disclosed in U.S. Pat. No. 5,717,212. Separate translation devices 22a, 22b, 22c, such as motors and drive assemblies, independently translate the detector heads radially and laterally in directions tangential to the subject receiving aperture 18 along linear tracks or other appropriate guides.

Each of the detector heads 20a–20c has a radiation receiving face facing the subject receiving aperture 18. Each head includes a scintillation crystal, such as a large doped sodium iodide crystal, that emits a flash of light or photons in response to incident radiation. An array of photomultiplier tubes receive the light flashes and convert them into electrical signals. A resolver circuit resolves the x, y-coordinates of each flash of light and the energy of the incident radiation. That is to say, radiation strikes the scintillation crystal causing the scintillation crystal to scintillate, i.e., emit light photons in response to the radiation. The photons are received by the photomultiplier tubes and the relative outputs of the photomultiplier tubes are processed and corrected to generate an output signal indicative of (i) a position coordinate on the detector head at which each radiation event is received, and (ii) an energy of each event. The energy is used to differentiate between various types of radiation such as multiple emission radiation sources, stray and secondary emission radiation, scattered radiation, transmission radiation, and to eliminate noise. In SPECT imaging, a projection image representation is defined by the radiation data received at each coordinate on the detector head. In PET imaging, the detector head outputs are monitored for coincident radiation events on two or more heads. From the position and orientation of the heads and the location on the faces at which the coincident radiation was received, a ray between the peak detection points is calculated. This ray defines a line along which the radiation event occurred. The radiation data from a multiplicity of angular orientations of the heads is then reconstructed into a volumetric image representation of the region of interest.

For SPECT imaging, the detector heads 20a–20c include mechanical collimators 24a, 24b, 24c, respectively, removably mounted on the radiation receiving faces of the detector heads 20a–20c. The collimators include an array or grid of lead vanes which restrict the detector heads 20a–20c from receiving radiation not traveling along selected rays in accordance with the selected imaging procedure. For PET imaging, a SPECT camera without collimators on the detector heads may be employed. Alternately, PET imaging is performed using collimators to minimize stray radiation.

Figure 2B:
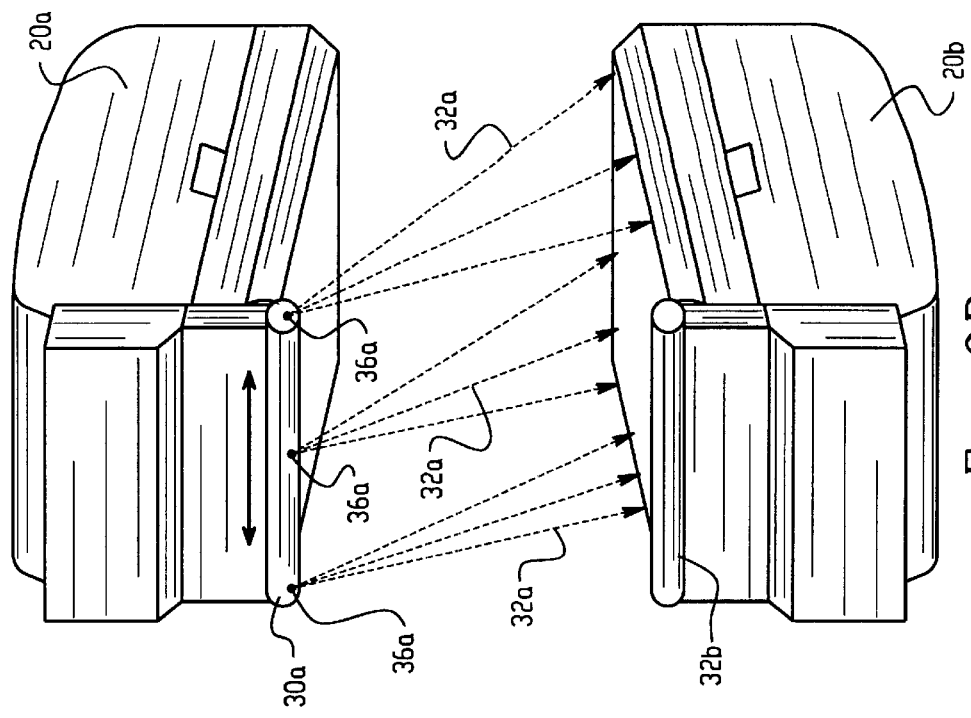
FIG. 2B is a perspective view of a preferred orientation of detector heads in a two head nuclear medicine gamma camera.
Figure 2A:
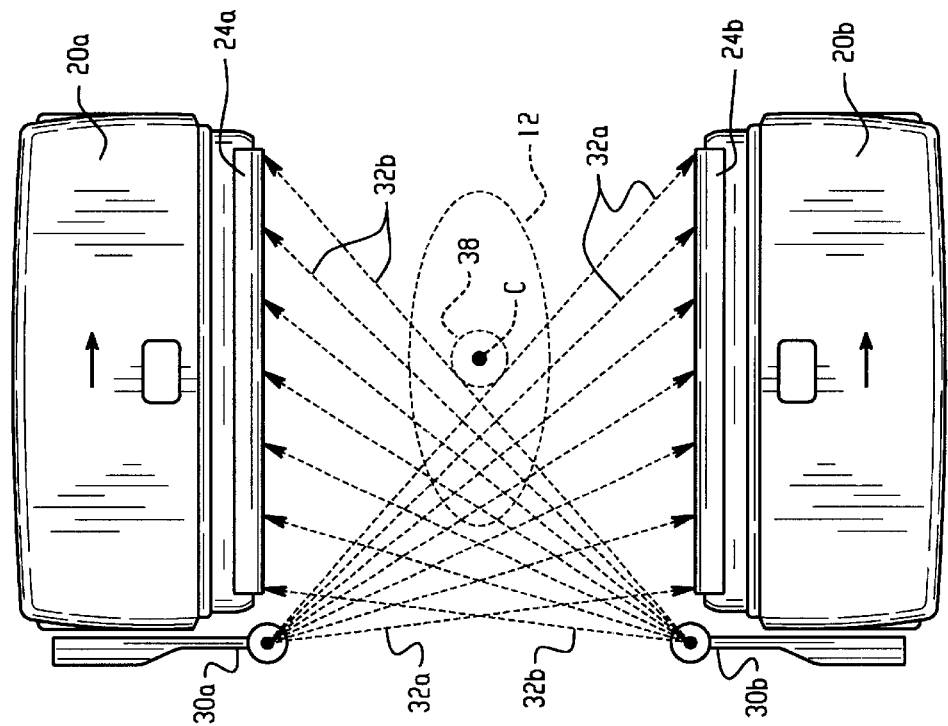
FIG. 2A is a side view of a preferred orientation of detector heads in a two head nuclear medicine gamma camera illustrating an unsampled region at the center of the subject.

FIG. 2A illustrates a two-head embodiment, including a first detector head 20a and a second detector head 20b arranged on the rotating gantry 16 on opposite sides of the subject receiving aperture 18 such that the radiation receiving faces of the first and second detector heads face one another. A first radiation source 30a is mounted to the first detector head 20a and is collimated such that transmission radiation (represented by the arrows 32a) from the radiation source 30a is directed toward and received by the second detector head 20b positioned across the subject receiving aperture from the radiation source 30a. A second radiation source 30b is mounted to the second detector head 20b and collimated such that transmission radiation 32b therefrom is directed toward and received by the first detector head 20a. The first and second radiation sources 30a, 30b are mounted at opposite ends of the radiation receiving faces of the first and second detector heads 20a, 20b as shown. The preferred collimators 24a, 24b are configured such that the detector heads 20a, 20b receive both the emission radiation and the transmission radiation 32a, 32b. That is to say, the collimators 24a, 24b restrict the detector heads 20a, 20b, (in the embodiment of FIG. 2A) from receiving those portions of transmission radiation not traveling along direct rays from the source to the radiation receiving faces of the detector heads. Alternately, other collimation geometries are employed for different applications and radiation sources, such as a line source. Additional collimation may take place at the source.

Figure 3:
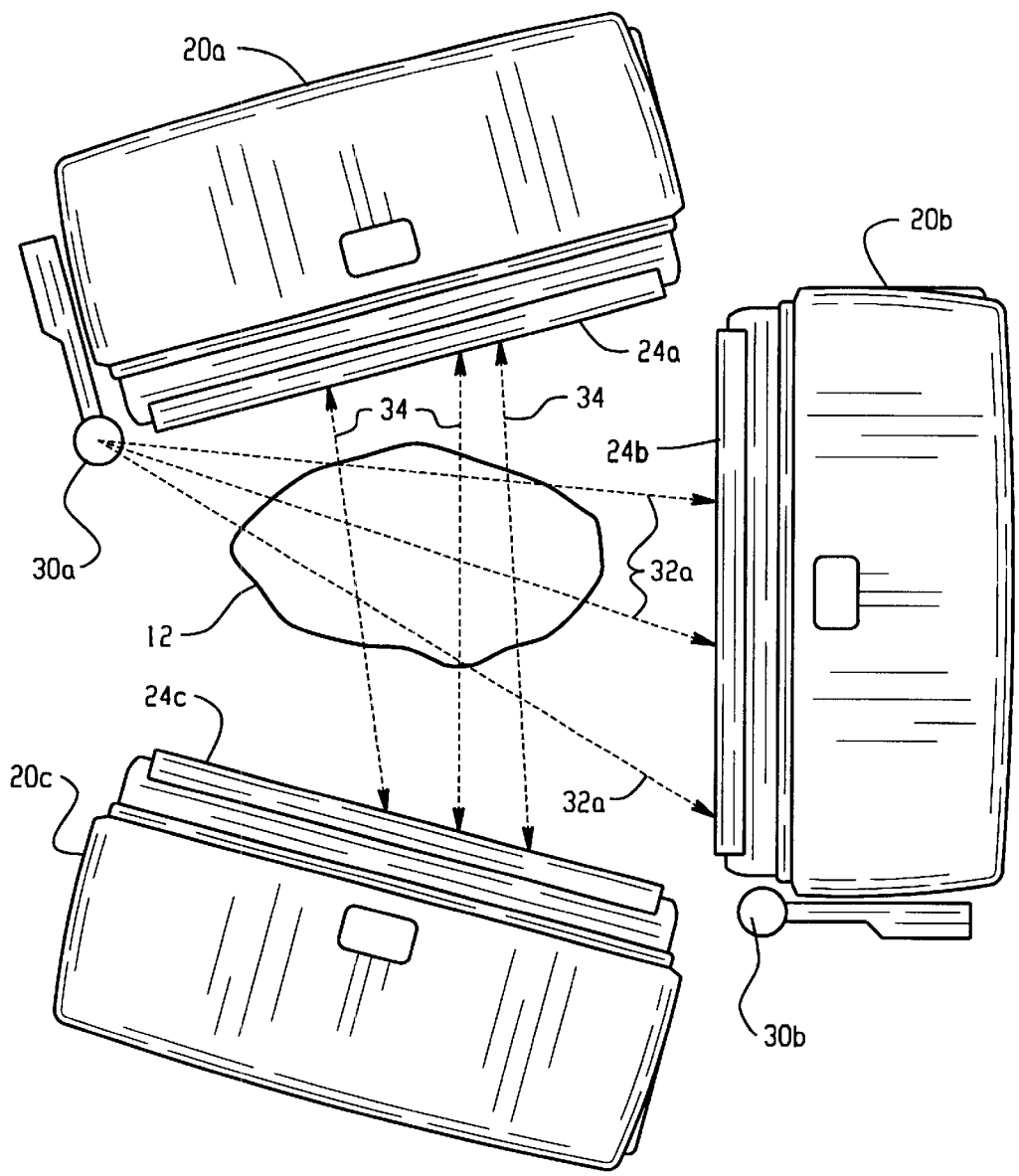
FIG. 3 is a diagrammatic illustration of a preferred orientation of detector heads in a three head nuclear medicine gamma camera in accordance with the present invention.

FIG. 3 illustrates a three-head embodiment, including a first detector head 20a, a second detector head 20b, and a third detector head 20c arranged on the rotating gantry 16 spaced from one another around the subject receiving aperture 18. A first radiation source 30a is mounted to the first detector head 20a such that transmission radiation 32a therefrom is directed toward and received by the second detector head 20b. A second radiation source 30b is optionally mounted to the second detector head 20b such that transmission radiation therefrom can be directed toward and received by the first detector head 20a. It is to be appreciated that radiation sources may be mounted to all three detector heads.

In one embodiment, the radiation source 30a contains a radioactive point source 36a adjustably mounted inside a shielded steel cylinder which is sealed at the ends. In this configuration, the radioactive point source generates a radiation fan beam which passes through the subject receiving aperture 18. As shown diagrammatically in FIG. 2B, as the radiation source 30a rasters longitudinally, the fan beam moves across the field of view. In a step and shoot mode, the transmission source undergoes a full raster (or integer number of rasters) at each step. In a continuous rotate mode, the fan beam spirals through the examination volume. The steel cylinder is adjustably mounted onto the corresponding detector head through a pivoting arm mechanism for retraction when the transmission source is not used. Alternately, the radiation source 30a is a bar source, flat rectangular source, disk source, flood source, tube or vessel filled with radionuclides, or active radiation generators such as x-ray tubes.

Figure 4A:
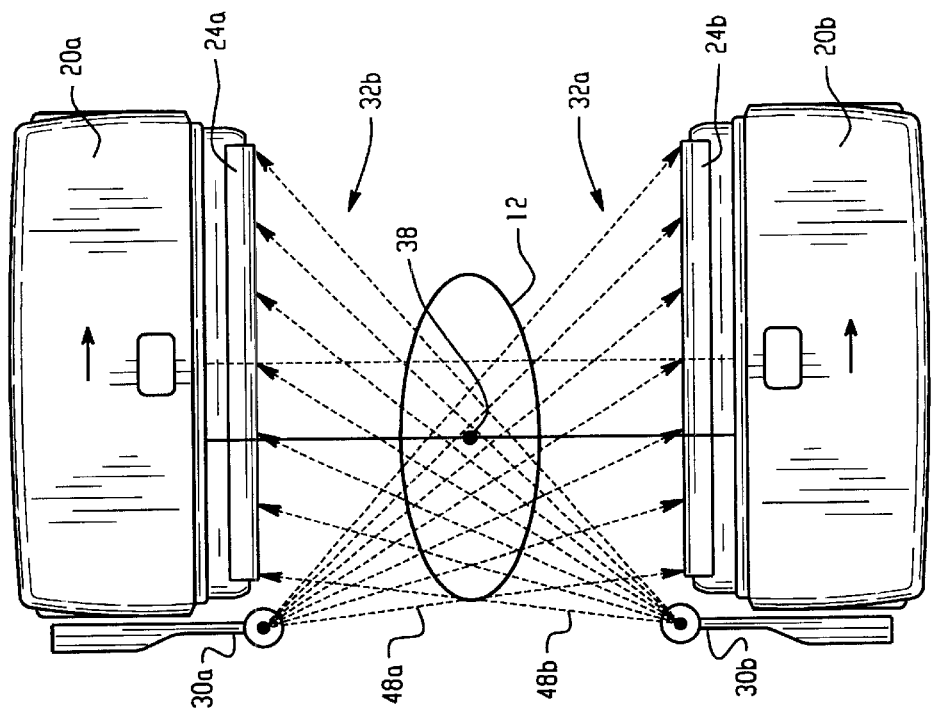
FIG. 4A is a side view of a preferred orientation of detector heads in a two head nuclear medicine gamma camera illustrating a minimal lateral shift in accordance with the present invention; and, FIG. 4B is a side view of a preferred orientation of detector heads in a two head nuclear medicine gamma camera illustrating an optimal lateral shift in accordance with the present invention.
Figure 4B:
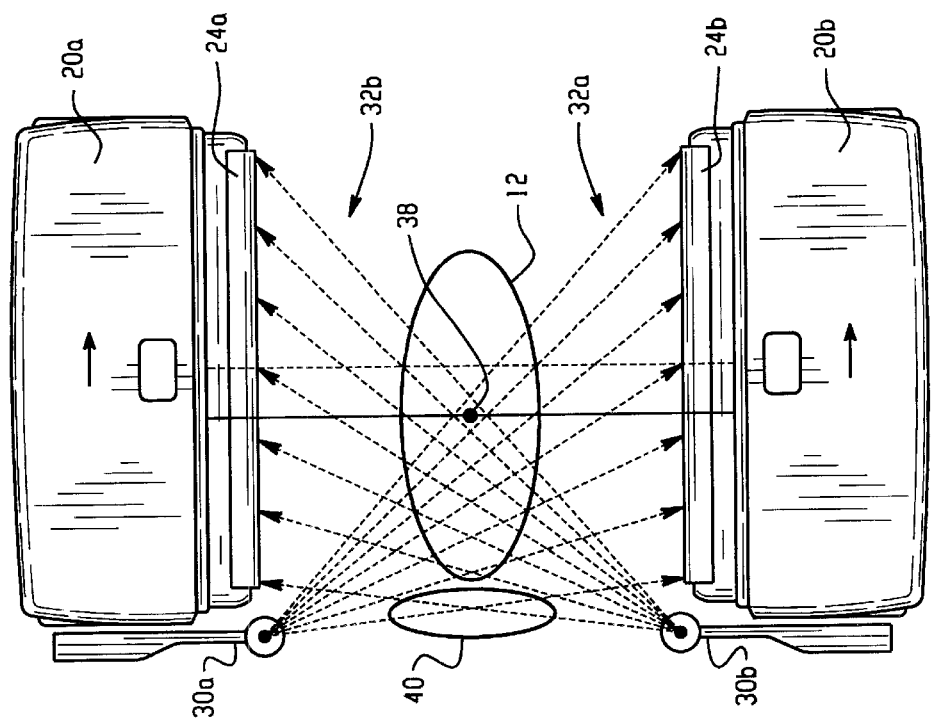

FIG. 2A illustrates the two-head embodiment in which the radiation sources 30a, 30b are mounted outside the field of view (FOV) of the first and second radiation detector heads 20a, 20b. Those skilled in the art will appreciate that having the radiation sources outside the FOV of the detector heads results in a "hole" or blind spot 38 in the transmission FOV. In other words, the transmission radiation from the first and second radiation sources does not pass through a region 38 surrounding a center C of the orbit. In order to receive that valuable transmission information from this central region 38, the detector heads 20a, 20b are shifted laterally, as shown in FIG. 4A, such that the transmission radiation fans 32a, 32b pass through the center C of the orbit. Shifting the detector heads 20a, 20b laterally just enough for the transmission radiation to pass through the center region of the FOV results in "lost rays" 40 which pass through air, rather than through the subject. In order to minimize or eliminate these lost rays 40 of transmission radiation, the detector heads are shifted further as shown in FIG. 4B. This optimal shift maximizes the portion of the transmission radiation fans 32a, 32b which pass through the subject being examined. The optimal shift is determined based on the location of virtual lines, which are described more fully below.

With reference again to FIG. 1, prior to running an imaging operation, the outer boundaries or contour of the subject 12 are defined and stored in an orbit memory 42. In one embodiment, the outer boundaries are entered manually into the orbit memory 42 based on the size of the subject. In another embodiment, the outer boundaries of the subject are determined during an initial contouring scan of the subject. During the contouring operation, the translation drives 22a–22c translate the detector heads laterally in directions tangential to the subject receiving aperture 18 and a contouring processor 44 calculates outer boundaries of the subject 12 based on the transmission radiation received by the detector heads. The edges of the subject are registered when the subject interferes with the transmission radiation emitted from the radiation sources as detected by the corresponding detector heads. That is to say, as the relative positions of the radiation sources and the corresponding detector heads are varied, the outer boundary of the subject interferes and/or crosses the path of the transmission radiation as it is transmitted across the subject receiving aperture. The rotating gantry is incrementally rotated with the contouring device 44 measuring the outer boundaries of the subject at a number of angular orientations to obtain a complete outer contour of the subject. A clearance offset calculator calculates a clearance offset 45, i.e., a minimum distance of approach between the head and the subject including the support.

Once the outer boundaries of the subject, including the clearance offset, are determined and stored in the orbit memory 42, a tangent calculator 46 calculates a first virtual line 48*a* between the first radiation source 30*a* and an edge of the second detector head 20*b*. Conversely, the tangent calculator calculates a second virtual line 48*b* between the second radiation source 30*b* and an edge of the first detector head 20*a*. These virtual lines 48*a*, 48*b* correspond to the end rays of the radiation fans generated by the first and second radiation sources 30*a*, 30*b*, respectively. It is to be appreciated that the virtual lines may be calculated based on the known geometry of the scanner. Once the virtual lines 48*a*, 48*b* are calculated by the tangent calculator 46, a shift calculator 50 calculates initial lateral shifts for each of the detector heads 20*a*, 20*b* as a function of angular position of the heads. The initial lateral shifts are determined such that each virtual line 48*a*, 48*b*, corresponding the end rays of each radiation fan 32*a*, 32*b*, is tangent to the predetermined orbit, corresponding to the outer boundaries or contour of the subject, as shown in FIG. 4B. As the imaging operation commences, a motor orbit controller 52 controls the rotational and translational drives 22*a*–22*c* moving the heads in and out with angular rotation to maintain the heads tangential to the clearance offset orbit and shifting the heads in response to shift inputs from the shift calculator 50. During the imaging operation, the shift calculator 50 determines lateral and radial shifts for each of the detector heads 20*a*–20*c* such that the positions of the detector heads are dynamically adjusted in order to maintain the virtual lines 48*a*, 48*b* tangent to the contour of the subject 12 throughout rotation of the gantry 16 around the subject receiving aperture 18. In other words, the mathematical relationship between the virtual lines and the predefined orbit around the patient is used to control lateral shifting of the detector heads throughout the acquisition of transmission radiation data. Artisans will appreciate that this technique maximizes the amount of transmission radiation which passes through the region of interest during a transmission scan by minimizing lost rays 40. Further, this technique is applicable to eliminate transmission data truncation caused by the edge of the predefined orbit being outside the end rays of the transmission radiation fan beam.

Maintaining the virtual lines tangent to the predefined orbit throughout the transmission scan adds a constraint on the detector heads in addition to keeping them moving along the oval orbit that defines the region of interest. From the perspective of the control software, namely the shift calculator 50 and motor orbit controller 52, the additional virtual line constraint is analogous to having a scanner with two additional "virtual detector heads" 48*a*, 48*b*. During an imaging operation the real detector heads 20*a*, 20*b* are dynamically adjusted according to constraints placed upon them and the positions of adjacent detector heads. For example, adjustment of a third virtual detector head 48*a*, corresponding to a virtual line from the first radiation source 30*a* to the second detector head 20*b*, results in a responsive adjustment of the real detector heads 20*a*, 20*b* based on the additional constraint.

Running an imaging operation includes a reconstruction process for emission and transmission data. The reconstruction process changes according to the type of radiation collected and the types of collimators used (i.e., fan, cone, parallel beam, and/or other modes). Emission radiation from the subject 12 is received by detector heads 20*a*–20*c* and transmission radiation 32*a*, 32*b* from the radiation sources 30*a*, 30*b* is received by the detector heads 20*a*, 20*b* to generate emission projection data and transmission projection data. The emission data normally contains inaccuracies caused by varying absorption characteristics of the subject's anatomy. A sorter 60 sorts the emission projection data and transmission projection data, such as on the basis of their relative energies or the detector head which originated the data. The data is stored in a projection view memory 62, more specifically in a corresponding emission data memory 62*e* and transmission data memory 62*t*. A reconstruction processor 64*t* uses a fan beam reconstruction algorithm to reconstruct the transmission data into a transmission image representation or volume of attenuation factors stored in a memory 66. Each voxel value stored in the memory 66 is indicative of attenuation of tissue in a corresponding location within the subject 12.

An emission data correction processor 68 corrects each emission data in accordance with the attenuation factors determined from the transmission data. More specifically, for each ray along which emission data is received, the emission correction processor 68 calculates a corresponding ray through the transmission attenuation factors stored in the memory 66. Each ray of the emission data is then weighted or corrected by the emission data correction processor 68 in accordance with the attenuation factors. The corrected emission data are reconstructed by an emission radiation reconstruction processor 70 to generate a three-dimensional emission image representation that is stored in a volumetric emission image memory 72. A video processor 74 withdraws selected portions of the data from the image memory 72 to generate corresponding human-readable displays on a video monitor 76. Typical displays include reprojections, selected slices or planes, surface renderings, and the like.

It is to be appreciated that the emission and transmission acquisition portions of the imaging operation need not be performed in a set order. In addition, emission and transmission radiation data may be acquired simultaneously.

Although positioning edge rays 48*a*, 48*b* tangent to the subject 12 is optimal for most applications, in some applications it may be desirable to over or undershift the heads. In the overshifted example, the heads are shifted such that the edge rays 48*a*, 48*b* are displaced a selected distance into the subject. The degree of such overshifting can be angularly dependent, e.g., deepest into the subject when the point of tangency is on the major axis and tangent or even displaced from the subject when the point of tangency lies on the subject's minor axis. In terms of constraints, the vertical heads 48*a*, 48*b* are constrained to be tangent to a different preselected orbit than the physical heads 20*a*, 20*b*. As yet another alternative, the edge rays can be monitored in real time by the detector heads or a separate edge ray detector and the shifting performed dynamically in real time based on monitored deviations from tangent.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear medicine gamma camera for diagnostic imaging, said gamma camera comprising:
    a rotating gantry which defines a subject receiving aperture;
    a plurality of radiation detector heads movably attached to the rotating gantry, said detector heads rotating about the subject receiving aperture with rotation of the rotating gantry about an axis of rotation;
    at least one radiation source mounted to the rotating gantry for rotation therewith, such that a divergent beam of transmission radiation from the at least one radiation source is directed toward and received by a corresponding detector head positioned across the subject receiving aperture from the radiation source;
    a rotational drive which rotates the plurality of detector heads around the subject receiving aperture;
    a plurality of translational drives which translate independently the plurality of detector heads (i) laterally in directions tangential to the subject receiving aperture and (ii) radially in directions orthogonal to the axis of rotation;
    an orbit memory which stores a predefined orbit which clears a subject disposed in the subject receiving aperture;
    a tangent calculator which calculates the position of a virtual line between the at least one radiation source and an edge of a radiation receiving face of the corresponding detector head which receives transmission radiation from the at least one radiation source;
    a shift calculator which calculates lateral and radial shifts for the plurality of detector heads such that the detector head positions are dynamically adjusted in order to maintain the virtual line tangent to an outer boundary of the subject throughout rotation of the gantry around the subject receiving aperture; and
    a motor orbit controller which controls the plurality of translational drives and the rotational drive in accordance with the orbit from the orbit memory and shift inputs from the shift calculator.

2. The nuclear medicine gamma camera according to claim 1, said gamma camera further comprising:
    a contouring device which determines outer boundaries of the subject disposed in the subject receiving aperture, the determined outer boundaries of the subject being stored in the orbit memory.

3. The nuclear medicine gamma camera according to claim 2, wherein the outer boundaries of the subject are determined prior to running an imaging operation.

4. The nuclear medicine gamma camera according to claim 1, wherein:
    the plurality of radiation detector heads includes a first detector head and a second detector head arranged on the rotating gantry on opposite sides of the subject receiving aperture such that radiation receiving faces of the first and second detector heads face one another; and,
    the at least one radiation source includes:
        a first radiation source mounted to the first detector head such that transmission radiation from the first radiation source is directed toward and received by the second detector head; and,
        a second radiation source mounted to the second detector head such that transmission radiation from the second radiation source is directed toward and received by the first detector head.

5. The nuclear medicine gamma camera according to claim 4, wherein the first and second radiation sources include:
    a radioactive point source contained within a shielded cylinder, said radioactive point source generating a plurality of transmission radiation fan beams.

6. The nuclear medicine gamma camera according to claim 5, wherein:
    the virtual line calculated by the tangent calculator corresponds to end rays of the transmission radiation fan beams.

7. The nuclear medicine gamma camera according to claim 6, wherein:
    the lateral shifts calculated by the shift calculator maximize the portion of the transmission radiation fan beams which pass through the subject disposed in the subject receiving aperture.

8. A method of diagnostic imaging using a nuclear medicine gamma camera, the method comprising:
    (a) placing a subject in a subject receiving aperture;
    (b) injecting the subject with a radiopharmaceutical;
    (c) positioning a plurality of radiation sources and corresponding radiation detector heads about the subject receiving aperture such that the radiation sources are across the subject receiving aperture from their corresponding radiation detector heads;
    (d) obtaining a contour of the subject disposed in the subject receiving aperture;
    (e) detecting radiation emitted by the injected radiopharmaceutical using the plurality of radiation detector heads;
    (f) calculating the position of virtual lines extending from each radiation source to an edge of a radiation receiving face disposed on each corresponding radiation detector head;
    (g) shifting the detector heads laterally such that the virtual lines are tangent to the contour of the subject;
    (h) transmitting radiation from the radiation sources toward the corresponding radiation detector heads positioned across the subject receiving aperture;
    (i) detecting radiation transmitted by the radiation sources using one of the plurality of radiation detectors; and
    (j) reconstructing the detected transmission and emission radiation into a volumetric image representation.

9. The method according to claim 8, wherein step (e) includes:
    rotating the radiation sources and corresponding radiation detector heads about the subject receiving aperture.

10. The method according to claim 9, wherein step (i) includes:
    rotating the detector heads and radiation sources about the subject receiving aperture; and
    dynamically adjusting the positions of the detector heads with radiation sources attached thereto in order to maintain the virtual lines tangent to the contour of the subject throughout rotation about the subject receiving aperture.

11. The method according to claim 10, wherein dynamically adjusting the detector heads includes translating the detector heads laterally in directions tangential to the subject receiving aperture.

12. The method according to claim 11, wherein step (j) includes:

reconstructing the detected transmission radiation into an attenuation volume image representation;

correcting emission radiation data using the attenuation volume image representation; and reconstructing the corrected emission radiation data into an emission volume image representation.

13. The method according to claim 12, wherein the correcting step includes:

calculating attenuation factors from the attenuation volume image representation, said attenuation factors corresponding to each ray along which emission data is received.

14. A nuclear camera system comprising:

a rotating gantry which defines a subject receiving aperture;

a plurality of real radiation detector heads movably attached to the rotating gantry, said real detector heads rotating about the subject receiving aperture with rotation of the rotating gantry about an axis of rotation;

a plurality of radiation sources mounted to the plurality of real detector heads for rotation with the rotating gantry, such that transmission radiation from the radiation sources is directed toward and received by the corresponding real detector heads positioned across the subject receiving aperture from the plurality of radiation sources;

a plurality of virtual detector heads, said virtual detector heads imposing shift restrictions on the real detectors heads during rotation about the subject receiving aperture;

a rotational drive which rotates the real detector heads around the subject receiving aperture;

a plurality of translational drives which translate independently the plurality of real detector heads at least one of laterally and radially with respect to the subject receiving aperture;

an orbit memory which stores a predefined contour of a subject disposed in the subject receiving aperture;

a shift calculator which calculates shifts in the real detector heads according to the predefined contour of the subject and the shift restrictions imposed by the virtual detector heads; and a motor orbit controller which controls the translational and rotational drives in response to commands from the shift calculator.

15. The nuclear camera system according to claim 14, said nuclear camera system further comprising:

a contouring device which determines outer boundaries of the subject disposed in the subject receiving aperture, the outer boundaries of the subject being stored in the orbit memory.

16. The nuclear camera system according to claim 15, wherein the plurality of radiation sources include:

a radioactive point source contained within a shielded cylinder, said radioactive point source generating a plurality of transmission radiation fan beams.

17. The nuclear camera system according to claim 16, wherein the virtual detector heads are located in positions corresponding to virtual lines which extend from the plurality of radiation sources to the corresponding real detector heads.

18. The nuclear camera system according to claim 17, wherein:

the virtual lines are calculated by a tangent calculator, said virtual lines corresponding to end rays of the transmission radiation fan beams.

19. The nuclear camera system according to claim 18, wherein:

the shift calculator calculates lateral shifts in order to maximize the portion of the transmission radiation fan beams which pass through the contour of the subject disposed in the subject receiving aperture.

20. A method of controlling a nuclear camera which includes a rotating gantry on which at least first and second detector heads are mounted, the first detector head carrying an offset transmission radiation source that projects a fan beam of transmission radiation to the second detector head, the fan beam extending between edge rays, a rotating drive which rotates the rotating gantry continuously or in steps, a radial drive which moves the detector heads in a radially inward direction toward a center of rotation of the rotating gantry and a radially outward direction away from the center of rotation, and a lateral drive which moves the detector heads with a component of motion orthogonal to the radially inward and outward directions, the method comprising:

positioning a subject on a subject support with a region of interest at the center of rotation;

calculating a clearance offset orbit around and displaced from the subject and the subject support;

calculating a subject orbit around the region of interest;

injecting the subject with a radiopharmaceutical;

controlling the rotating drive and the radial drive such that the detector heads are maintained tangent to the clearance offset orbit as the detector heads are rotated around the subject; and controlling the lateral drive such that one of the fan beam edge rays is maintained tangent to the subject orbit as the detector heads rotate.

21. The method according to claim 20, wherein the subject orbit is coincident with a circumference of the subject.

* * * * *